United States Patent [19]

Aoshiro

[11] Patent Number: 4,860,631
[45] Date of Patent: Aug. 29, 1989

[54] OUTER TUBULAR ENVELOPE FOR INSERTING APPARATUS

[75] Inventor: Hisatake Aoshiro, Misato, Japan

[73] Assignee: Kabushiki Kaisha Machida Seisakusho, Japan

[21] Appl. No.: 187,503

[22] Filed: Apr. 28, 1988

Related U.S. Application Data

[63] Continuation of Ser. No. 918,149, Oct. 14, 1986, abandoned.

[30] Foreign Application Priority Data

Apr. 16, 1986 [JP] Japan ................... 61-56090

[51] Int. Cl.$^4$ ................... D04C 1/06; D04C 1/02
[52] U.S. Cl. ................... 87/9; 33/719; 33/755; 87/6
[58] Field of Search ................... 87/1, 6-9; 33/169 R, 169 B, 302, 544, 126.5, 719, 720, 755; 138/123-127, 130

[56] References Cited

U.S. PATENT DOCUMENTS

| | | | |
|---|---|---|---|
| 1,104,777 | 7/1914 | Cobb | 138/124 X |
| 2,335,088 | 11/1943 | Shoemaker | 87/9 X |
| 2,924,141 | 2/1960 | Kinniburgh | 87/9 |
| 3,073,209 | 1/1963 | Benk et al. | 87/6 |

FOREIGN PATENT DOCUMENTS 863837 3/1961 United Kingdom ................... 87/9

*Primary Examiner*—John Petrakes
*Attorney, Agent, or Firm*—Kane, Dalsimer, Sullivan, Kurucz, Levy, Eisele and Richard

[57] ABSTRACT

An outer tubular envelope for covering an elongated inserting portion of an inserting apparatus such as, for example, an endoscope. A plurality of strands are braided into the form of a tube. At least one of the strands is different in color from the remaining strands and is woven thereinto so as to extend helically at a constant pitch.

7 Claims, 1 Drawing Sheet

OUTER TUBULAR ENVELOPE FOR INSERTING APPARATUS

This is a continuation of co-pending application Ser. No. 918,149 filed on Oct. 4, 1986, now abandoned.

BACKGROUND OF THE INVENTION

The present invention relates to an outer tubular envelope for covering an elongated inserting portion of an inserting apparatus such as, for example, an endoscope or the like.

In recent years, an industrial endoscope has widely been utilized to inspect an interior of a piping or a machine, in view of such advantage that the interior of the piping or machine can be viewed without disassembling the same.

A general endoscope comprises an operating body, an ocular portion provided at the operating body, and an elongated flexible inserting portion extending from the operating body. The inserting portion is inserted into an interior of an object to be inspected, and the interior of the object is viewed by the ocular portion through an optical viewing system incorporated in the inserting portion.

The conventional inserting portion has an outer peripheral surface thereof covered with an outer tubular envelope formed of a rubber material. However, such outer envelope formed of a rubber material is high in frictional resistance, and this often makes it difficult to insert the inserting portion into the object to be inspected.

In view of the above, it has been proposed that a plurality of strands formed of a slippery material such as, for example, extremely fine steel wires are braided into the form of a tube to form an outer tubular envelope, and the inserting portion is covered with such envelope The outer envelope has an outer peripheral surface thereof which is graduated by paints or inks at constant intervals, to allow an operator to determine a length of the inserting portion inserted into an object to be inspected, in use.

However, the graduations of paints or inks are disadvantageous in that the graduations are rubbed off and disappear, in the course of rubbing against the object to be inspected, during the use for a long period of time.

OBJECT AND SUMMARY OF THE INVENTION

An object of the present invention is to provide an outer tubular envelope for covering an elongated inserting portion of an inserting apparatus, which can stably be used, for a long period of time, as graduations for determining a length of the inserting portion inserted into an object.

According to the invention, there is provided an outer tubular envelope for covering an elongated inserting portion of an inserting apparatus, the outer tubular envelope comprising:

a plurality of stands braided into the form of a tube; and at least one of the strands being different in color from the remaining strands and incorporated therein so as to extend helically at a substantially constant pitch.

DETAILED DESCRIPTION

Embodiments of the invention will now be described with reference to the drawings.

Figure 1:
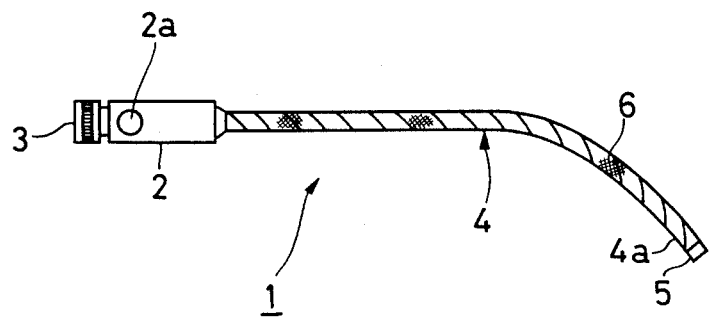
FIG. 1 is a diagrammatic view showing an endoscope having an elongated inserted portion which is covered with an outer tubular envelope according to the invention.

Referring to FIG. 1, there is shown in endoscope 1 to which the invention is applicable. The endoscope 1 comprises an operating body 2, an ocular portion 3 provided at one end of the operating body 2 and an elongated flexible inserting portion 4 extending from the operating body 2. The inserting portion 4 has, adjacent a distal end thereof, a bendable section 4a having a curvature which is remotely controllable by a dial 2a at the operating body 2. A hard or rigid tip component 5 is provided at an end of the bendable section 4a adjacent the distal end of the inserting portion 4. The tip component 5 has an end face provided therein with a viewing window and an illuminating window, both not shown. The viewing window is optically connected to the ocular portion 3.

Figure 2:
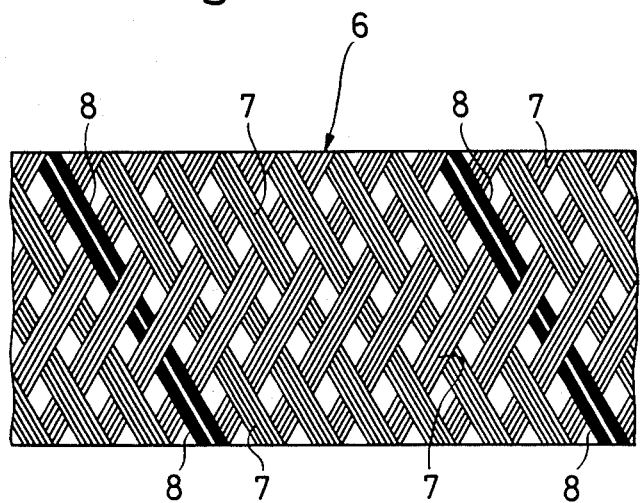
FIG. 2 is a fragmental enlarged view of the outer tubular envelope illustrated in FIG. 1.

The inserting portion 4 has an outer peripheral surface thereof which is covered with an outer tubular envelope 6. As shown in FIG. 2, the outer envelope 6 is formed in such a manner that a plurality of strands comprised of a plurality of bundles of extremely fine silver steel wires 7 and a single bundle of red nylon threads 8 are braided into the form of a tube. Specifically, thirteen bundles of a plurality of steel wires 7 and a single bundle of a plurality of nylon threads 8 are prepared; and a group of six bundles of steel wires 7 and a single bundle of nylon threads 8 and a group of seven bundles of steel wires 7 are braided so as to be intersected with each other.

Stitches of the respective bundles of steel wires 7 and nylon threads 8 are inclined with respect to a longitudinal axis of the outer envelope 6. Accordingly, as the inserting portion 4 is covered with the outer envelope 6, the bundle of nylon threads 8 extends helically at a constant pitch which is determined depending upon the angle of intersection between the aforesaid groups, a ratio in bundle between the steel wires 7 and the nylon threads 8, and the like.

In the operation of the endoscope 1 constructed as described above, the inserting portion 4 is inserted into an interior of an object to be inspected, through an opening provided in the object, and the interior of the object is viewed by the ocular portion 3. During the insertion of the inserting portion 4 into the object through the opening therein, an operator can count the number of pitches of the bundle of nylon threads 8 inserted into the object, to thereby determine a length of the inserting portion 4 inserted into the object.

The bundle of nylon threads 8 is red in color, whereas the bundles of steel wires 7 are silver in color. This enables the operator to clearly identify the bundle of nylon threads 8, to thereby effectively prevent the operator from failing to recognize the bundle of nylon threads 8.

In addition, since the bundle of nylon threads 8 together with the bundles of steel wires 7 is incorporated into a tube, it is minimized that the bundle of nylon threads 8 is rubbed off and disappears, unlike the conventional graduations of paints or inks, and can be used as graduations for a long period of time.

Figure 3:
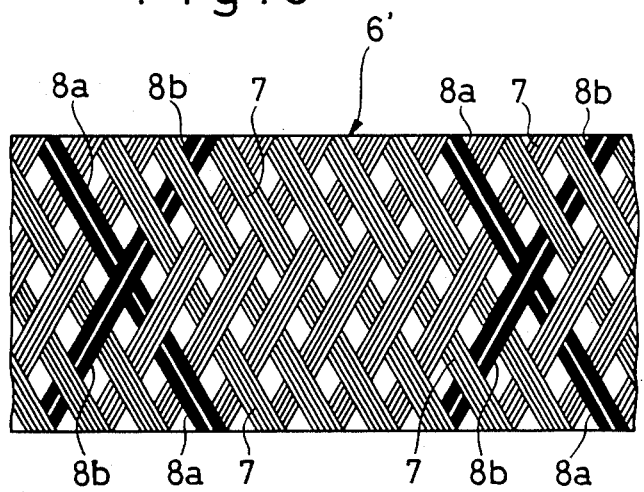
FIG. 3 is a view similar to FIG. 3 but showing an outer tubular envelope according to another embodiment of the invention.

FIG. 3 shows an outer tubular envelope 6' in accordance with another embodiment of the invention. In FIG. 3, like reference numerals are used to designate parts or components similar to those shown in FIG. 2, and such similar parts or components will not therefore be described in detail here to avoid repetition. The outer envelope 6' is formed in such a manner that a group of six bundles of steel wires 7 and a single bundle of nylon threads 8a and a group of another six bundles of steel wires 7 and another single bundle of nylon threads 8b are braided so as to be intersected with each other. Thus, as the inserting portion 4 shown in FIG. 1 is covered with the outer envelope 6', the bundle of nylon threads 8a in one of the aforesaid two groups extends helically at a constant pitch in a first direction, and the bundle of nylon threads 8b in the other group extends helically in a second direction opposite to the first direction, at a constant pitch equal to that of the bundle of threads 8a.

In the another embodiment shown in FIG. 3, points of intersection between the bundles of nylon threads 8a and 8b form graduations which are counted by an operator to determine a length of the inserting portion 4 inserted into an object to be inspected.

The invention should not be limited to the specific embodiments described above, but various changes and modifications can be made to the invention. For example, a combination in color of the strands is not limited to the combination of red and silver, but may be any one of various combinations which enable an operator to identify both strands.

In addition, the materials of the strands are not limited to the steel and nylon, but may be selected from various kinds of materials. For example, the strands may be formed of steel wires and copper wires, or of the same material as far as colors are different from each other.

Moreover, the outer envelope in accordance with the embodiments of the invention may be used to cover an outer peripheral surface of a guide tube which is inserted into an object to be inspected, antecedent to the inserting portion of the endoscope, to guide the inserting portion into the object.

As described above, according to the invention, at least one strand different in color from the remaining strands extends at a constant pitch helically around an inserting portion of an inserting apparatus. This makes it possible for an operator to count the number of pitches of the at least one strand, to thereby determine a length of the inserting portion inserted into an object.

The at least one strand having the different color is, together with the remaining strands, braided into a tube. Accordingly, it can be minimized that the at least one strand is rubbed off and disappears, unlike the paints or inks. This makes it possible to use the at least one strand as graduations for a long period of time.

In addition, the application of the graduations to the envelope can be achieved only by knitting the strands. This eliminates the necessity that a work or operation of applying graduations to an envelope is done after the formation of the envelope, as is the case with the conventional envelope. This also improves the productivity.

What is claimed is:

1. An endoscope comprising:
   an operating body;
   an elongated inserting portion extending from said operating body; and
   an outer tubular envelope with which said elongated inserting portion is covered, said outer tubular envelope having a plurality of strands braided into the form of a tube, at least one of said strands being different in color from the remaining strands and being incorporated therein so as to extend helically at a substantially constant pitch to define graduations for determining a predetermined length of the inserting portion inserted into an object.

2. An endoscope according to claim 1, wherein two of said strands are different in color from the remaining strands and are incorporated therein, a first one of said two strands extending helically in a first direction at a substantially constant pitch, and a second one of said two strands extending helically in a second direction opposite to said first direction, at a substantially constant pitch equal to that of said first strand, to form a plurality of points of intersection.

3. An endoscope according to claim 1, wherein at least one strand is formed of a resinous material, and said remaining strands are formed of a metallic material.

4. An endoscope according to claim 3, wherein at least one strand is comprised of a bundle of nylon strands, and said remaining strands are comprised of a plurality of bundles of steel wires.

5. An endoscope according to claim 1, wherein at least one strand is red in color, while said remaining strands are silver in color.

6. An endoscope according to claim 1, wherein at least one strand helically extends over the entire length of the outer tubular envelope.

7. An endoscope according to claim 1, wherein said elongated inserting portion is flexible.

* * * * *